(12) United States Patent
Saraç et al.

(10) Patent No.: US 10,342,896 B2
(45) Date of Patent: Jul. 9, 2019

(54) BIOACTIVE NANOFIBER CYTO-SCAFFOLD

(71) Applicant: ISTANBUL TEKNIK ÜNIVERSITESI REKTÖRLÜĞÜ, Istanbul (TR)

(72) Inventors: Abdulkadir Sezai Saraç, Istanbul (TR); Zeliha Güler, Istanbul (TR)

(73) Assignee: ISTANBUL TEKNIK ÜNIVERSITESI REKTÖRLÜĞÜ, Istanbul (TR)

( * ) Notice: Subject to any disclaimer, the term of this patent is extended or adjusted under 35 U.S.C. 154(b) by 54 days.

(21) Appl. No.: 15/686,147

(22) Filed: Aug. 24, 2017

(65) Prior Publication Data

US 2018/0055970 A1 Mar. 1, 2018

(30) Foreign Application Priority Data

Aug. 26, 2016 (TR) .............. a 2016 12096

(51) Int. Cl.

| | |
|---|---|
| A61K 38/06 | (2006.01) |
| A61L 27/18 | (2006.01) |
| C07K 5/09 | (2006.01) |
| C08G 63/08 | (2006.01) |
| C08G 69/12 | (2006.01) |
| A61L 27/22 | (2006.01) |
| C08L 77/10 | (2006.01) |
| A61K 9/00 | (2006.01) |

(52) U.S. Cl.
CPC .............. *A61L 27/18* (2013.01); *A61K 38/06* (2013.01); *A61L 27/227* (2013.01); *C07K 5/0817* (2013.01); *C08G 63/08* (2013.01); *C08G 69/12* (2013.01); *C08L 77/10* (2013.01); *A61K 9/0024* (2013.01); *A61L 2400/12* (2013.01)

(58) Field of Classification Search
None
See application file for complete search history.

(56) References Cited

PUBLICATIONS

Chaisri et al., "Repetitive Arg-Gly-Asp peptide as a cell-stimulating agent on electrospun poly($\epsilon$-caprolactone) scaffold for tissue engineering," Biotechnol. J. 8:1323-1331 (2013) (Year: 2013).*
Wisse et al. "Multicomponent Supramolecular Thermoplastic Elastomer with Peptide-Modified Nanofibers", Journal of Polymer Science Part A: Polymer Chemistry, Mar. 2011, vol. 49, 1764-1771.
Fang Jian et al. "Applications of electrospun nanofibers", Chinese Science Bulletin, Aug. 2008, vol. 53, No. 15, 2265-2286.
E. Sachlos et al. "Making Tissue Engineering Scaffolds Work. Review on the Application of Solid Freeform Fabrication Technology to the Production of Tissue Engineering Scaffolds", European Cell and Materials, 2003, vol. 5, 29-40.
Zhang X et al. "Electrospun silk biomaterial scaffolds for regenerative medicine", Advanced Drug Delivery Reviews, 2009, 61, 988-1006.
Spagnuolo M et al. "Fabrication and Degradation of Electra spun Scaffolds from L-tyrosine Based Polyurethane Blends for Tissue Engineering Applications," ISRN Nanotechnology vol. 2012, Article ID 627420, 11 pages; doi:10.5402/2012/627420.
Nisbet D. R. et al. "A Review of the Cellular Response on Electro spun Nanofibers for Tissue Engineering", Journal of Biomaterials Applications, 2009, 24, 7-29.
Wenfu Zheng et al. "Biometic Collagen Nanofibrous Materials for Bone Tissue Engineering" Advanced Engineering Materials, 2010, 12, 9, B451-B466.
Soh-Zeom Yow et al. "A 3D Electroactive Polypyrrole-Collagen Fibrous Scaffold for Tissue Engineering", Polymers, 2011, 3, 527-544.
Mengyan Li et al."Electrospinning polyaniline-contained gelatin nanofibers for tissue engineering applications", Biomaterials, 2006, 27, 2705-2715.
Ravichandran R et al. "Applications of conducting polymers and their issues in biomedical engineering", J. R. Soc. Interface, 2010, 7, S559-S579.
Plessis D.M. "Fabrication and characterization of anti-microbial and biofouling resistant nanofibers with silver nanoparticles and immobilized enzymes for application in water filtration", Master's Thesis, University of Stellenbosch, Faculty of Science Department of Biochemistry, 2011.
Avci Z.M. et al. "Transparent Poly(methyl methacrylate-co-butyl acrylate) Nanofibers", J. Appl. Polym. Sci. 2013, DOI: 10.1002/APP.39705, pp. 4264-4272.

* cited by examiner

*Primary Examiner* — Julie Ha
*Assistant Examiner* — Kristina M Hellman
(74) *Attorney, Agent, or Firm* — Gokalp Bayramoglu

(57) ABSTRACT

The invention relates to obtaining nanofibers that contain biocompatible polymers and using the product obtained by making them bioactive through linking covalent proteins to said nanofibers in tissue engineering.

11 Claims, 5 Drawing Sheets

BIOACTIVE NANOFIBER CYTO-SCAFFOLD

CROSS REFERENCE TO RELATED APPLICATIONS

This application is based upon and claims priority to Turkey Patent Application No. TR 2016/12096, filed on Aug. 26, 2016, the entire contents of which are incorporated herein by reference.

FIELD OF THE INVENTION

The invention relates to obtaining nanofibers that contain biocompatible polymers and using the product obtained by making them bioactive through linking covalent proteins to said nanofibers in tissue engineering.

BACKGROUND

Bioactive nanofibers are a new and fast-growing study field that has a high application potential in biomedical fields such as tissue engineering, drug and gene release and biosensor applications. The studies in the biomaterials field have been considerably advanced by using biocompatible and biodegradable materials with materials having bioactivity. Bioactivity becomes useful especially in tissue engineering studies [Wisse, E. Spiering, A. J. H., Dankers, P. Y. W., Mezari, B., Magusin, P. C. M. M., Meijer, E. M., J. Of Pol. Sci. Part A:Pol. Chem. 1764-1771, (2011)].

Tissue or organ loss is a significant health problem and there are lots of problems experienced in traditional treatment methods. The object of the tissue engineering studies; is to enable fixing, replacing or improving the function of certain tissues and organs by overcoming the limitations experienced in the traditional methods. The tissue engineering studies that comprise implementation of a functional, natural, synthetic or semi-synthetic tissue or organ imitation create an alternative or complementary solution potential for traditional methods [Tian, F., Tao, N. H., Tong, T., Gai, W. X., Applications of electro spun nanofibers, Chinese Science Bulletin, 53, 15, 2265-2286, (2008)].

In tissue engineering studies the cells are in vitro seeded on a scaffold. The cells proliferate on the scaffold, migrate and differentiate to specific tissues by secreting extracellular matrix (ECM) components required for formation of the tissue [Sachlos, E., Czernuszka, J. T., Making Tissue Engineering Scaffolds Work. Review On The Application Of Solid Freeform Fabrication Technology To The Production Of Tissue Engineering Scaffolds, European Cell And Materials, 5, 29-40, (2003)]. For tissue engineering to be successful, the scaffold that will provide structural support to the cells and cell-matrix (scaffold) interactions that will govern the tissue growth shall be emphasized. The scaffold structure plays a key role in tissue engineering since it mimics the natural ECM structure. The scaffold that serves as the temporary support during the time until the cells from natural ECM provides chemical, morphologic and structural signals for formation of the targeted tissue [Zhang, X., Reagan, M. R., Kaplan, D. L., Electro spun silk biomaterial scaffolds for regenerative medicine, Advanced Drug Delivery Reviews, 61, 988-1006, (2009)].

In tissue engineering, the material that will be used in scaffold design must be biocompatible, biodegradable and in a porous structure having a high surface area [Spagnuolo, M., Karpuz, O., Liu, L., Fabrication and Degradation of Electro spun Scaffolds from L-tyrosine Based Polyurethane Blends for Tissue Engineering Applications, Journal of Nanotechnology, (2011)]. Nanofibers have a high specific area and excellent pore connections due to their small fiber diameters. The scaffolds formed by nanofibers are ideal structures for being used in tissue engineering applications since they mimic ECM fibril structure and since they provide signals that stimulate cellular organization, vitality and function [Nisbet, D. R., Forsythe, J. S., Review Paper: A Review Of The Cellular Response On Electro spun Nanofibers For Tissue Engineering, Journal Of Biomaterials Applications, 24, 7-29, (2009)].

A bioactive molecular cell migration such as a specific peptide or growth factor may stimulate processes such as growth or differentiation. Therefore, it is possible to obtain bioactive nanofibers by binding bioactive molecules to nanofiber mats obtained through electrospinning method. Electrospinning method is particularly suitable for obtaining bioactive polymer nanofibers. This method is simple and inexpensive for large scale production. In addition, nanofibers provide a larger surface area and thus more protein loading capacity when compared to protein immobilized polymer film surfaces. Bringing bioactivity to polymers is performed by mixing the bioactive molecules and polymer solutions or by covalently binding the biomolecule to the polymer via functional groups. However, mixing the bioactive molecule with the polymer solution is not an efficient method since it does not allow controlling the activity of the molecule and it does not allow the molecule to bind to the desired region. In this situation, a covalent bond is advantageous [Wisse, E. Spiering, A. J. H., Dankers, P. Y. W., Mezari, B., Magusin, P. C. M. M., Meijer, E. M., J. Of Pol. Sci. Part A:Pol. Chem. 1764-1771, (2011)].

In making the polymer nanofibers functional by using covalent binding with proteins, usually the existence of carboxylic acid groups in the polymer structure is utilized. For this purpose, water soluble agents 1-ethyl-3-(3-dimethyl aminopropyl)carbodiimide hydrochloride (EDC) and N-hydroxysulfosuccinimide (sulfo-NHS) are commonly used. EDC that has low toxicity enables the formation of amide bonds between the carboxylic acid groups and amino groups. They are used in the covalent binding of biomolecules on polymers by being used together with NHS [Zheng, W., Zhang W., Jiang, X., Biometic Collagen Nanofibrous Materials for Bone Tissue Engineering, ADVANCED ENGINEERING MATERIALS, 12, 9, B451-B466, (2010)].

Nanofibers are obtained from various different polymers as synthetic or natural. In tissue engineering studies, the nanofiber structures that are obtained by electrospinning method from poly(lactic acid) (PLA), poly(glycolic acid) (PGA), poly(ε-caprolactone) (PCL) and poly(α-hydroxyl acid) group polymers that are copolymers thereof are frequently used in making scaffolds [Yow, S. Z., Lim, T. H., Yim, E. K. F., Lim, C. T., Leong, K. W., A 3D Electroactive Polypyrrole-Collagen Fibrous Scaffold for Tissue Engineering, Polymers, 3, 527-544, (2011)].

Using conductive polymers in tissue engineering studies stands as a new approach [Li, M., Guo, Y., Wei, Y., MacDiarmid, A. G., Lelkes, P. I., Electrospinning polyaniline-contained gelatin nanofibers for tissue engineering applications, Biomaterials, 27, 2705-2715, (2006)]. Conductive polymers have the potential of governing the adhesion, migration, protein secretion and DNA synthesis functions of cells that respond to electrical stimulation such as nerve, bone, muscle and cardiac cells. The conductivity of the conductive polymers that are a special class of materials having electronic and ionic conductivity is originating from the conjugated double bonds in the polymer backbone

[Ravichandran, R., Sundarrajan, S., Venugopal, J. R., Mukherjee, S., Ramakrishna, S., Applications of conducting polymers and their issues in biomedical engineering, J. R. Soc. Interface, 7, S559-S579, (2010)]. Using pyrrol, thiophene and aniline derived from the heteroaromatic monomers and conductive polymers which are derivatives thereof gains a substantial interest in tissue engineering. However, since said biocompatible and conductive polymers do not have regions on their surfaces that help cell recognition, it limits the use of nanofiber mats obtained from said polymers in various biomedical fields such as tissue engineering applications.

Therefore, in order to increase biocompatibility and make nanofibers gain biofunctionality, bioactive molecules can be included into the nanofiber scaffold. It is known that including RGD peptide and various growth factors into the nanofiber mats increases the cell behavior and adhesion in tissue engineering scaffolds [Plessis, D. M, Fabrication and characterization of anti-microbial and biofouling resistant nanofibers with silver nanoparticles and immobilized enzymes for application in water filtration, (Master's Thesis), University of Stellenbosch, Faculty of Science Department of Biochemistry, (2011)]. Ravichandran et al. (2010) covalently bound the RGD peptide (Arg-Gly-Asp) to the polypyrol layer obtained by electropolymerization and enabled use of the polymer in orthopedic applications as a bioactive material (Ravichandran, R., Sundarrajan, S., Venugopal, J. R., Mukherjee, S., Ramakrishna, S., Applications of conducting polymers and their issues in biomedical engineering, J. R. Soc. Interface, 7, S559-S579, (2010)]. The carboxyl groups (—COOH) in the aspartic acid (Asp) amino acid that is present in the RGD peptide structure have the ability to make a covalent bond with a polymer having chemically active parts.

In the invention, production and detailed characterization of conductive and bioactive nanofiber mats that have a high potential of use in tissue engineering field is realized. Accordingly, in situ polymerization of the poly(m-anthranilic acid) (P3ANA) conductive polymer in polycaprolactone (PCL) solution which is a biocompatible polymer is realized. Nanofiber mats are produced by electrospinning method from the obtained polymer solution. P3ANA contains carboxyl group in the aniline backbone and has a great potential of use due to its processability in aqueous, nonaqueous and polar solvents [Avci, Z. M., Sarac, A. S., Transparent Poly(methyl methacrylate-co-butyl acrylate) Nanofibers, J. Appl. Polym. Sci. (2013) DOI: 10.1002/APP.39705]. By utilizing the presence of —COOH group in the P3ANA structure, the RGD peptide (Arg-Gly-Asp) that is a cell adhesion protein will covalently bind to the nanofiber mat by using the 1-ethyl-3-(3-dimethylaminopropyl) carbodiimide hydrochloride (EDC) and N-hydroxysulfosuccinimide (sulfo-NHS) agents and the mat is made bioactive.

SUMMARY

The invention comprises polymer based nanofiber mat production and making the nanofiber mat functional by covalent immobilization of the biomolecules. The nanofibers have high specific area due to their small fiber diameters and provide the support required for cell growth. Cell interaction can be increased by inclusion of a bioactive molecule such as a specific peptide or growth factor into the nanofiber structure. Even though the biomolecule is included into the nanofibers in various ways, the covalent binding which is the method used in development of the product is an efficient method since it allows the molecule to bind to the desired region and since it allows controlling the activity of the molecule. The product of the invention increases the success rate of use of the product in tissue engineering by increasing the nanofiber-cell interaction through obtaining nanofibers containing biocompatible polymers and making them bioactive via binding proteins to said nanofibers covalently.

Since the product of the invention contains conductive polymers, the bioactivation of the nanofibers with proteins can get thinner by electrochemical impedance method. In the invention, using the nanofiber mat containing conductive polymers provides an advantage both in the stage where the surface is not modified by biomolecule and in the stage where electrochemical measurement is performed during the determination of the analyte. In contrast to the traditional methods, the electrochemical impedance spectroscopy (EIS) method is quite successful in determination of the surface modifications and is a method that can perform identification in high precision and selectivity after the electrode surface is made functional by a unique biomolecule.

REFERENCE NUMERALS

Figure 1:
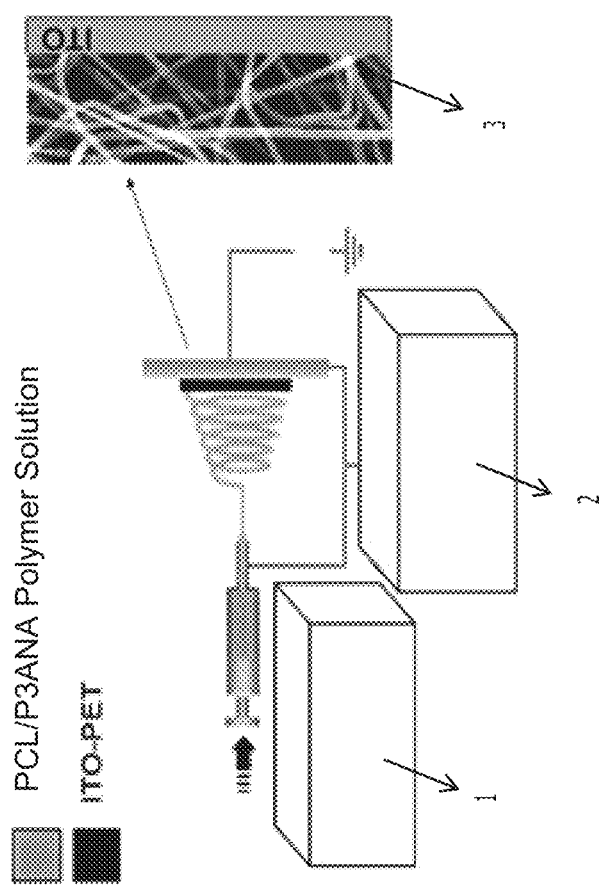
FIG. 1: Fabrication of PCL/P3ANA nanofibers by electrospinning method.
Figure 2:
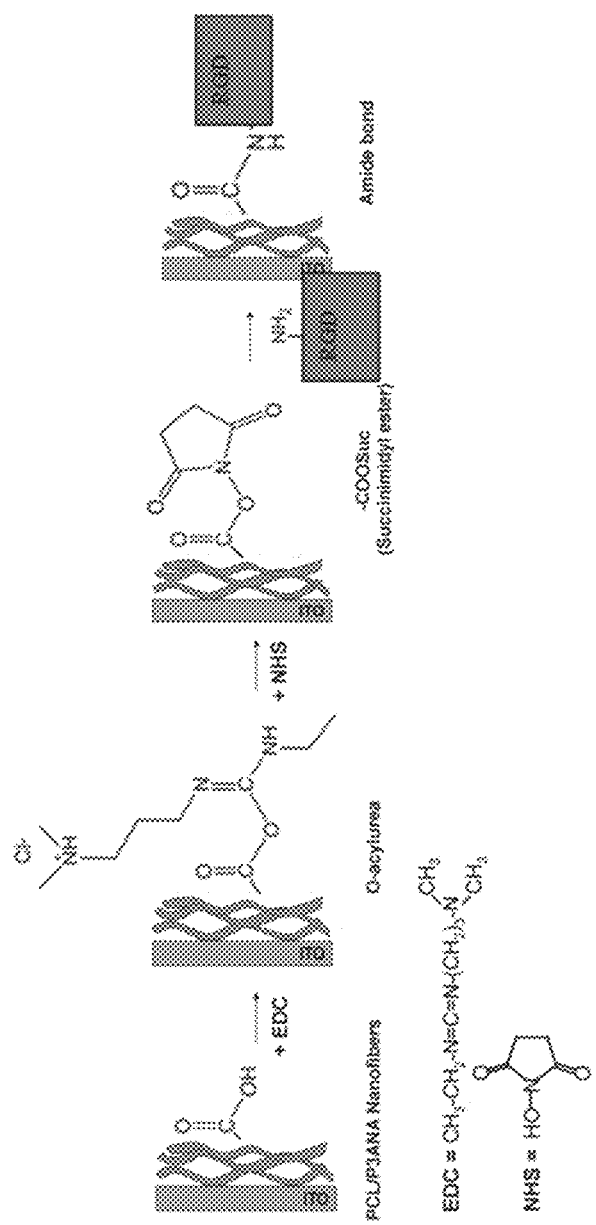
FIG. 2: Covalent binding of RGD peptide to the nanofibers by EDC-NHS method.

1. Syringe Pump
2. High voltage source
3. Nanofiber mat.

DETAILED DESCRIPTION

In the bioactive nanofiber cyto scaffold of the invention, PCL/P3ANA nanofibers are produced by electrospinning method comprising the following steps:

First, dissolving 15% by weight poly(caprolactone) (PCL) into a tetrahydrofuran/dimethylformamide (THF/DMF, 1:1 by volume) solution.

Obtaining an electro spun solution by adding 15% by weight P3ANA to the PCL solution with respect to the previously synthesized PCL.

Loading the PCL/P3ANA solution into a syringe, the syringe is preferably a 23 G needle, 5 ml volume syringe having an outer diameter of 0.7 mm.

Placing the syringe containing the PCL/P3ANA solution into a electrospinning device and connected to the high voltage direct current (DC) source.

Applying a 10-20 kV voltage to the polymer solution and said voltage is preferably 15 kV.

Wherein a distance between a needle tip of the syringe and a collector is kept fixed and said distance is preferably 15 cm.

Feed rate of the solution is set to 1 mL/h by a syringe pump.

Covalently immobilizing the RGD peptide is to the P3ANA/PCL nanofibers by using carbodiimide binding reaction.

Fresh preparing agents comprising an 1-ethyl-3-(dimethyl-aminopropyl) carbodiimide hydrochloride (EDC) and an N-hydroxysuccinimide (NHS) just before the reaction in cold a 0.1 M 2-(n-morpholino) ethansulfonic acid (MES) in one to one molar proportion and preferably in 10 mg/ml concentration.

Activating the prepared nanofiber mat by shaken incubation with the EDC/NHS solution for 1.5 to 2.5 hours, preferably for 2 hours at room temperature between 100 rpm and 300 rpm, preferably at 200 rpm.

Washing the activated nanofiber mat by shaking with the MES buffer for 5-15 minutes, preferably for 10 minutes and by between 100-300 rpm, preferably at 200 rpm.

Activating the washed nanofibers by shaken incubation in the MES buffer containing the RGD peptide for 1.5-2.5 hours, preferably for 2 hours at room temperature between 100-300 rpm, preferably at 200 rpm.

Nanofiber mat surface is washed twice by shaking with MES buffer for 5-15 minutes, preferably for 10 minutes and between 100-300 rpm, preferably at 200 rpm for removing the RGD peptide molecules that may physically attach to the surface.

PCL and P3ANA ratio in the composition of the nanofiber of the invention can be changed to allow nanofiber yield by electrospinning method. ITO-PET provides physical support to the PCL/P3ANA nanofibers. The nanofibers are yielded on the ITO-PET to enable reproducibility of the electrochemical measurements. During the cell experiments, the nanofibers on the ITO-PET or just the nanofibers can be used. PCL/P3AAN nanofibers can serve as cytoscaffold. Instead of ITO-PET, the nanofiber can be obtained on a different support material such as glass, FTO-glass (fluorine doped tin oxide coated glass) or ITO-glass.

Bioactivation of the nanofibers by RGD peptide is proved through electrochemical impedance spectroscopy. Electrochemical impedance spectroscopy measurements are performed by an electrochemical measurement device (potentiostat) and triple electrode system is used in the measurements. In this triple electrode system; the product of the invention (PCL/P3ANA-RGD) is used as the working electrode, silver (ag) wire is used as reference electrode and platinum (Pt) electrode is used as the counter electrode. EIS measurements are performed at room temperature in 0.1M phosphate buffer (PBS) with a pH value of 7.4 between 0.01 Hz and 100 kHz frequency range and by applying 10 mV alternative current.

Embodiment 1: Yield of PCL/P3ANA Nanofibers on ITO-PET by Electrospinning Method PCL/P3ANA polymer solution is loaded into the syringe (outer diameter 0.7 mm, with 23 G needle) and the nanofibers are obtained by applying 15 kV DC voltage at 1 mL/hour feed rate on the aggregator placed 15 cm away. In order to provide physical support to the nanofiber mat and to increase the strength of the obtained electrode, the nanofibers are aggregated on the semi-conductive ITO-PET (Indium tin oxide coated Polyethylene terephthalate film).

Embodiment 2: Covalent Binding of the RGD Peptide on the PCL/P3ANA Nanofibers

Carboxyl groups contained within the structure of the nanofibers incubated in the 1-ethyl-3-(dimethyl-aminopropyl) carbodiimide hydrochloride (EDC) and N-hydroxysuccinimide (NHS) solution is activated. One double bond of the Carbodiimide (EDC) chemical is added to the —OH group in the carboxyl group present in the nanofiber structure and O-acylurea product is formed then this product is converted to succinimide ester (—COOSuc) product in the presence of NHS. Succinimidylesterreacts with the primer amine (—NH$_2$) in the RGD peptide structure and RGD peptide binds to the nanofibers covalently.

Embodiment 3: FTIR-ATR Characterization of PCL, PCL/P3ANA (FIG. 3A) and RGD Bound Nanofibers (FIG. 3B)

Figure 3:
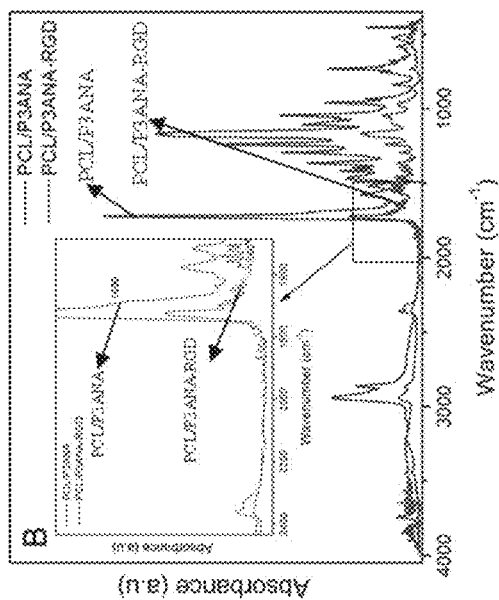
FIG. 3: FTIR-ATR spectra of PCL, PCL/3ANA nanofibers (A) and RGD peptide bound nanofibers (B).
Figure 3:
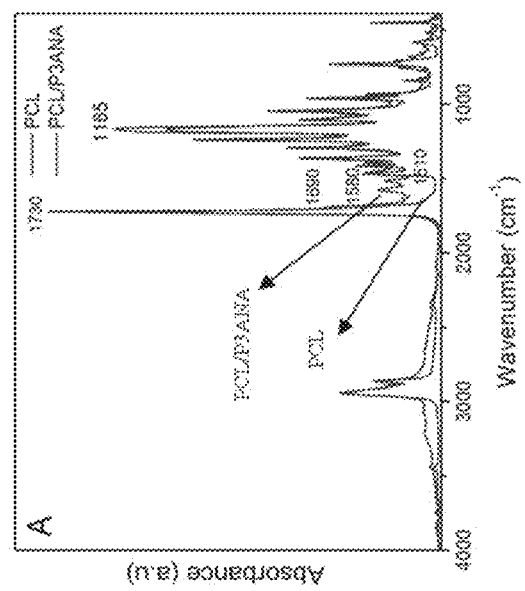

In FIG. 3A, the peak value of the C=O groups in the PCL nanofibers is seen at 1730 cm$^{-1}$. After addition of P3ANA to the nanofiber structure new peaks can be seen at 1690 cm$^{-1}$, 1580 cm$^{-1}$ and 1510 cm$^{-1}$ belonging to P3ANA respectively as C=O stretching, C=C stretching and N—H stretching which are not present in the PCL structure. In FIG. 3B, FTIR-ATR graph obtained after binding of the RGD peptide to the nanofiber is shown. In the FTIR spectrum, 1700-1600 cm$^{-1}$ is a region sensitive to the protein structure. The peak seen at 1560 cm$^{-1}$ in the FTIR spectrum represents the N—H bond in the RGD structure. Moreover, the peaks seen at 1740 cm$^{-1}$, 1650 cm$^{-1}$ and 1540 cm$^{-1}$ belong respectively to the C=O stretching in the ester group, Amid I C=O stretching and N—H deformation in Amid II in the RGD structure.

Figure 4:
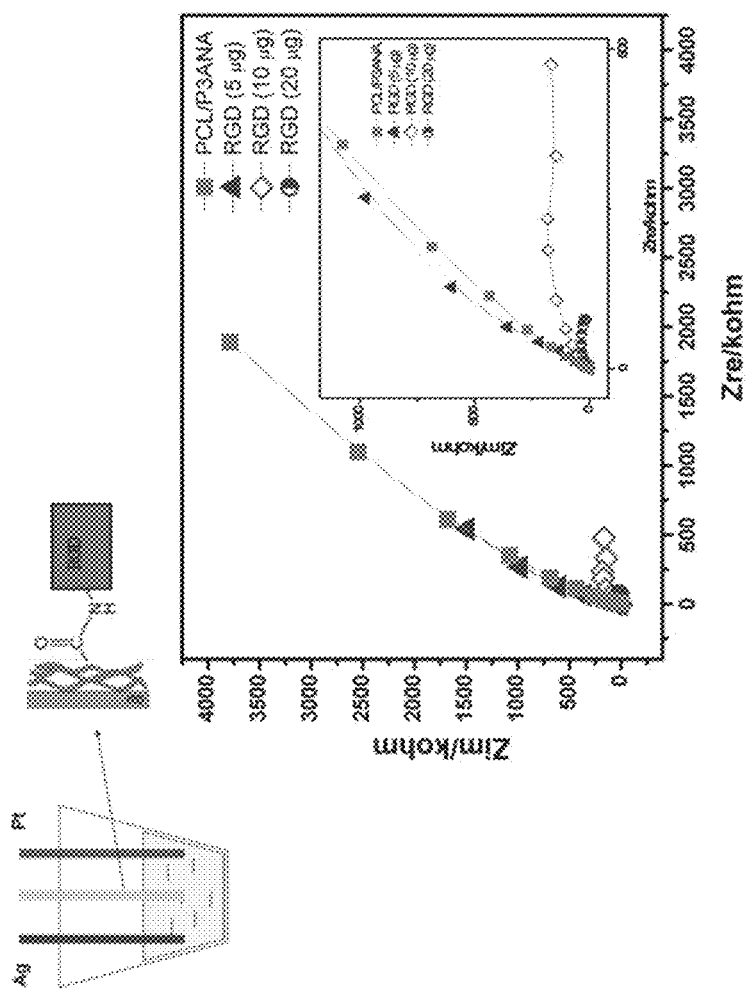
FIG. 4: EIS measurement schematic view (top), Nyquist plot of RGD peptide bound PCL/P3ANA nanofibers.
Figure 5:
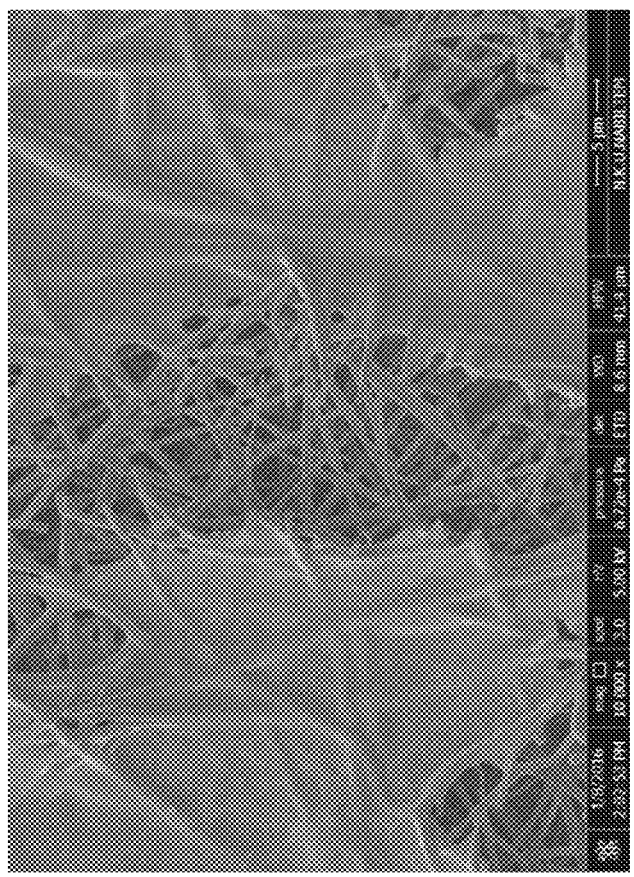
FIG. 5: SEM view of cells being grown on PCL/P3ANA-RGD nanofibers.

Embodiment 4: EIS Measurements and Analysis Related to RGD Peptide Bound PCL/P3ANA Nanofibers During EIS measurement triple electrode system (PCL/P3ANA or PCL/P3ANA-RGD nanofibers produced in the invention as working electrode, silver (Ag) wire as reference electrode and platinum (Pt) electrode as the counter electrode) is used (FIG. 4—top). In the Nyquist graph of the PCL/P3ANA nanofibers, a significant difference is seen after binding of the RGD peptide to the nanofibers. The radius obtained by the points where the semi-circle obtained from the Nyquist graph given in FIG. 4 (bottom) intersects the x axis represents the charge transfer resistance (Rct) and the linear part represents the capacitive behavior. While PCL/P3ANA nanofibers have a linear Nyquist graph, semi-circular curves are obtained in Nyquist graphs obtained after covalent binding of the RGD peptide. This situation suggests that RGD peptide increases the resistance of the nanofibers. This increase in the charge transfer resistance is described by formation of a layer that is blocking ion transfer on the nanofiber surface by the RGD peptide molecules.

Embodiment 5: SEM Image of Cells Grown on PCL/P3ANA-RGD Nanofibers

The cells are grown on the nanofiber for 9 days and distribution and growth of the cells on the nanofiber is shown by SEM. At the end of 9th days, the cells are spread on the nanofiber surface and grown. SEM image shows that PCL/P3ANA-RGD nanofibers are biocompatible and promotes cell reproduction.

What is claimed is:
1. A bioactive nanofiber comprising a poly(m-anthranilic acid) (P3ANA), a poly(caprolactone) (PCL) and an arginine-glycine-aspartic acid (RGD) peptide.
2. An electrospinning method for producing a bioactive nanofiber, comprising the following steps:

dissolving 15% by weight of PCL (poly(caprolactone)) in a tetrahydrofuran:dimethylformamide (THF/DMF) solution, wherein the volume ratio of THF to DMF is 1:1, obtaining electro spun solution by adding 15% by weight of P3ANA (poly(m-anthranilic acid)) with respect to PCL into the PCL solution to obtain a PCL/P3ANA solution, loading the PCL/P3ANA solution into a syringe, placing the syringe into an electrospinning device, applying a voltage between 10-20 kV to the PCL/P3ANA solution in the syringe, setting a feed rate of the PCL/P3ANA solution to obtain a P3ANA/PCL nanofiber onto a collector, covalently immobilizing RGD (arginine-glycine-aspartic acid) peptide to the P3ANA/PCL nanofiber by carbodiimide binding reaction, to obtain a nanofiber mat, freshly preparing an EDC/NHS solution comprising an 1-ethyl-3-(dimethyl-aminopropyl) carbodiimide hydrochloride (EDC) and an N-hydroxysuccinimide (NHS) before a reaction in a cold 0.1 M 2-(n-morpholino) ethansulfonic acid (MES) in one to one molar proportion, activating the nanofiber mat with the EDC/NHS solution by shaken incubation for 1.5 hours to 2.5 hours at room temperature between 100 rpm and 300 rpm to obtain activated nanofiber mats, washing the activated nanofiber mats twice by shaking with MES buffer for 5-15 minutes and between 100-300 rpm to obtain washed nanofibers, activating the washed nanofibers by shaken incubation in the MES buffer containing RGD peptide for 1.5 hours to 2.5 hours at room temperature between 100 rpm and 300 rpm to obtain an activated washed nanofiber, and washing a nanofiber mat surface of the activated washed nanofiber twice by shaking with MES buffer for 5-15 minutes and between 100-300 rpm for removing RGD peptide molecules physically attached to the nanofiber mat surface.

3. The method according to claim 2, wherein a distance between a needle tip of the syringe and the collector is maintained at a fixed distance.

4. The method according to claim 2, wherein a distance between the needle tip of the syringe and the collector is 15 cm.

5. The method according to claim 2, wherein the feed rate of the PCL/P3ANA solution is set to 1 mL/h.

6. The method according to claim 2, wherein the prepared nanofiber mats are activated by being shaken and incubated with the EDC/NHS solution for 2 hours at room temperature, 200 rpm.

7. The method according to claim 2, wherein the activated nanofiber mats are washed with MES buffer twice by shaking at 200 rpm, 10 minutes respectively.

8. The method according to claim 2, wherein the washed nanofibers are activated by being shaken at 200 rpm and incubated in the MES buffer comprising RGD peptide for 2 hours at room temperature.

9. The method according to claim 2, wherein the nanofiber mat surface is washed by being shaked with the MES buffer twice at 200 rpm for 10 minutes respectively to remove the RGD peptide molecules physically attached to the nanofiber mat surface.

10. The method according to claim 2, wherein a 15 kV voltage is applied to the PCL/P3ANA solution in the syringe.

11. An RGD peptide immobilized PCL/P3ANA bioactive nanofiber obtained by the method according to claim 2.

* * * * *